United States Patent [19]

Chirife

[11] Patent Number: 4,865,036
[45] Date of Patent: Sep. 12, 1989

[54] ANTITACHYARRYTHMIA PACEMAKER USING PRE-EJECTION PERIOD TO DISTINGUISH PHYSIOLOGIC FROM PATHOLOGIC TACHYCARDIA

[76] Inventor: Raul Chirife, Pirovano 137, 1640 Marinez, Buenos Aires, Argentina

[21] Appl. No.: 205,463

[22] Filed: Jun. 10, 1988

[51] Int. Cl.⁴ .............................................. A61N 1/36
[52] U.S. Cl. ........................ 128/419 D; 128/419 PG; 128/703
[58] Field of Search ............. 128/419 PG, 419 D, 703

[56] References Cited

U.S. PATENT DOCUMENTS 4,773,401 9/1988 Citak et al. .................... 128/419 PG Primary Examiner—Lee S. Cohen
Assistant Examiner—Scott Getzow
Attorney, Agent, or Firm—Orrin M. Haugen; Thomas J. Nikolai; Frederick W. Niebuhr

[57] ABSTRACT

A cardiac stimulator apparatus for effecting cardioversion or defibrillation in the event of pathologic tachycardia or ventricular fibrillation in which the rate of heart depolarization signals is compared to a predetermined heart rate value indicative of the onset of tachycardia while, simultaneously, the heart's pre-ejection period is monitored to sense whether an increase in heart rate above the predetermined value is accompanied by a decrease in the pre-ejection period. If not, a pathologic rather than a physiologic episode is diagnosed and a cardioversion pulse protocol is initiated. By also monitoring the mechanical pulse of the heart, if an inordinately high heart rate is accompanied by a low or non-existing mechanical pulse, ventricular fibrillation is diagnosed and the cardioverter is triggered to shock the heart back into sinus rhythm. If the mechanical pulse rate tracks the electrical rate of depolarization, tachyarrythmia is confirmed. The diagnosis may be further confirmed by taking into account the rate at which the heart rate increases.

6 Claims, 2 Drawing Sheets

ANTITACHYARRYTHMIA PACEMAKER USING PRE-EJECTION PERIOD TO DISTINGUISH PHYSIOLOGIC FROM PATHOLOGIC TACHYCARDIA

BACKGROUND OF THE INVENTION

I. Field of the Invention

This invention relates generally to cardiac electrical stimulation apparatus, and more particularly to apparatus for detecting irregular heartbeat action and for intervening with appropriate stimulation to suit the nature of the particular arrythmia encountered.

II. Discussion of the Prior Art

Many forms of cardiac pacing apparatus are known in the art for treating irregular heartbeat action. These include the relatively simple asynchronous pacemakers as well as various types of more elaborate demand pacemakers. The asynchronous pacemaker merely generates pulses at a fixed rate and is not generally synchronized with the heart's own rate. In the demand pacemaker, the device remains dormant when cardiac activity is normal. However, it includes a means for sensing the absence of a normal beat and, in response, injects artificial stimulating pulses at the appropriate point in the cardiac cycle to thereby maintain near-normal rhythms. Such demand pacers have become very sophisticated with advances in microelectronics which has combined high-complexity circuitry with small physical size and low power consumption. Heart activity can be sensed in both the atrium and ventricles, allowing stimulation to be provided on a demand basis, to either or both the atrium and ventricle and in proper timed relation to mimic the normal cardiac cycle. Such pacemakers are commonly prescribed in treating various types of heart block and bradycardias.

One form of stimulator which has received somewhat less attention is that designed to distinguish between normal high heart rate due to physical or emotional activity (physiologic tachycardia) and abnormal high heart rates not based on physiologic demand (pathologic tachycardia). Pathologic tachycardia results in inefficient pumping of blood by the heart and often may revert to lethal episodes of cardiac fibrillation.

Antitachycardia pacemakers have been used with some success in treatment of supraventricular tachyarrythmias which were found not to respond to drugs. Ventricular tachycardia and fibrillation are far more difficult to diagnose by a pacemaker algorithm, and an error in diagnosis may be, in itself, fatal to the patient. This is especially true in the situation where an incorrect diagnosis is made in connection with a patient in whom an automatic antitachycardia pacemaker or a defibrillator is implanted. A defibrillatory, high-energy discharge or a burst of pacing impulses could be applied to the patient inappropriately. If a defibrillating pulse is applied when not needed, it is wasteful of battery power and highly disconcerting to the patient. If an antitachycardia pulse or pulse pattern is applied and it falls into the vulnerable period, it may, in itself, precipitate ventricular tachycardia or fibrillation.

In prior art systems, the factors used in the algorithm for diagnosis of tachyarrythmias have all been related to the heart's electrical signal. Typically, they may include the R-wave repetition rate, the time interval over which the increase in rate takes place and QRS duration. Each of these factors can be simulated by myopotentials, electromagnetic interference, supraventricular tachyarrythmias and bundle branch block or even physiologic sinus tachycardia with or without aberrant A-V conduction. Thus, a need exists for an antitachyarrythmia pacer which can more accurately distinguish between physiologic and pathologic tachycardias.

The present invention provides a method and apparatus for reliably detecting the onset of pathologic tachycardia and for initiating the operation of a cardioversion pulse generator when an inappropriately high rate is detected. The cardioversion pulse generator then produces a pattern of pulses for capturing the heart and bringing the rate into a safe range appropriate to the metabolic condition of the subject at the time.

SUMMARY OF THE INVENTION

The operation of the present invention is premised on the fact that since physiologic increments of heart rate are always accompanied by a corresponding shortening of the pre-ejection period (PEP), it can be safely assumed that whenever there is a fast pulse rate with a relatively long PEP, that rate is due to a non-physiologic tachycardia, such as a paroxysmal ventricular or supraventricular tachycardia due to a re-entry mechanism. The simultaneous measurement of heart rate and PEP therefore permits discrimination between abnormal supraventricular tachycardias and physiologic sinus tachycardia, such as occurs during physical exercise or in any other situation where catecholamines are released into the bloodstream.

More particularly, co-existence of a rapid mechanical pulse rate together with a rapid QRS rate provides information which significantly improves the efficacy of an automatic diagnosis of tachyarrythmia. For example, if no pulse exists at the same time that rapid electrical activity is occurring, it is a strong indicator of ventricular fibrillation. If the mechanical pulse is rapid and the QRS rate is also high, there is a lesser likelihood that electrical noise or myopotentials are involved.

As is set out in the Chirife U.S. Pat. No. 4,719,921, the teachings of which are hereby incorporated by reference, it is well known that the pre-ejection period (PEP) is a faithful indicator of the sympathetic activity upon the heart. The direct action of the sympathetic nerve on the heart causes an acceleration of rate as well as a simultaneous increase in contractility. The same holds true for the effects of catecholamines released by the adrenals due to increased sympathetic tone. It is known that there is a close parallelism between the normal atrial response to catecholamines and sympathetic tone and the duration of the PEP. It has been shown that both dynamic and isometric exercise results in a shortening of the PEP. If increases in heart rate are due to reasons other than physical effort and not mediated through sympathetic action or catecholamines release, there is no corresponding shortening of the PEP. This can be shown by subjecting a patient to atrial or ventricular pacing when he or she is at rest, such that there is an artificial increment in heart rate with the PEP being found to remain essentially constant in length.

Thus, by monitoring pulse rate and PEP, pathologic and physiologic tachycardias can be readily distinguished. For example, if it is found that a rapid increase in pulse rate is accompanied by a shortening of the PEP, physiologic tachycardia can be presumed. Where, however, an increase in pulse rate above a predetermined reference level is accompanied by a stable PEP, it indicates pathologic tachycardia. An inordinately high R- wave rate with no measurable mechanical pulse indicates ventricular fibrillation.

The reliability of the diagnosis of pathologic tachycardia can be increased when the rate of increase in heart rate is factored into the detection algorithm. In normal sinus rhythm, stable atrial fibrillation or in gradually increasing heart rates occasioned by exercise, the comparison at two different instants in time only a few seconds apart would not be expected to result in substantial differences. For example, the sum of 10 R-R cycle lengths should be similar to another sum of 10 R-R cycles lengths when taken a few seconds apart. If the difference is greater than a predetermined percentage, it is implied that a sudden change has occurred. If such a sudden change is not similarly accompanied by a corresponding reduction in the length of the pre-ejection period, a sudden onset pathologic tachycardia is diagnosed and a burst cardioversion can be initiated. The synchronization of the burst pulses with the R-waves is carried out in a conventional fashion known in the art.

Summarizing, then, for burst cardioversion to take place, the following conditions must be met:

1. Sudden-onset tachycardia;
2. An equally rapid cardiac mechanical (pulse) response must occur; and
3. The tachycardia not be accompanied by a proportional shortening of PEP.

On the other hand, if the sudden-onset tachycardia is detected as well as he loss of a previously existing mechanical pulse, ventricular fibrillation is indicated whereby a defibrillating shock may be delivered by the implanted stimulator.

In accordance with the present invention, an artificial electronic cardiac stimulator is adapted to sense tachyarrythmia episodes and distinguish between physiologic tachycardia, pathologic tachycardia and ventricular fibrillation whereby appropriate stimulation can be developed for performing cardioversion, or where necessary, defibrillation.

The foregoing objectives and advantages of the invention will become more apparent from the following detailed explanation of an illustrative embodiment as set forth in the accompanying drawings.

DESCRIPTION OF A PREFERRED EMBODIMENT

Figure 1:
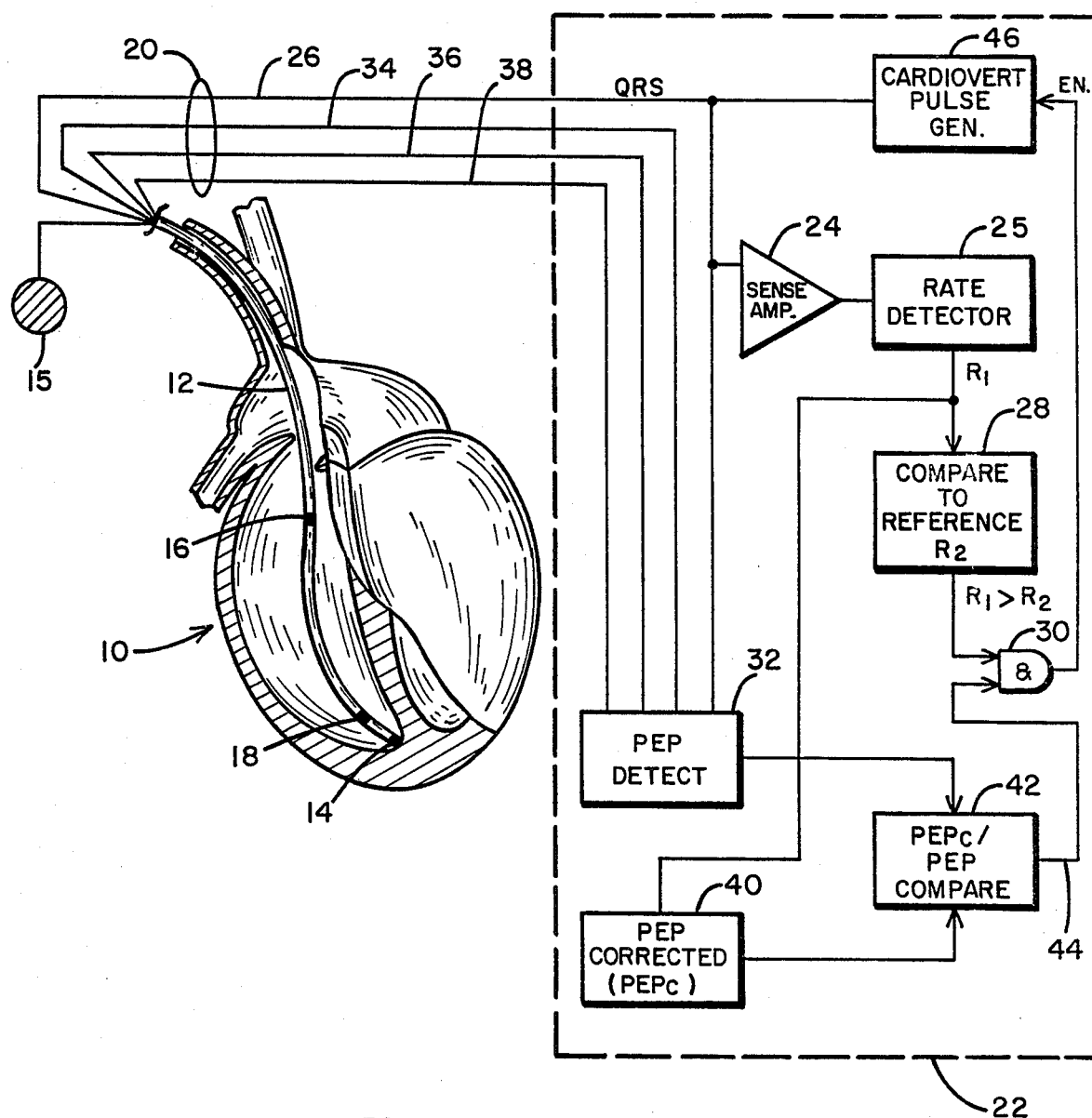
FIG. 1 is a block diagram useful in explaining a first embodiment of the present invention.

The rather simplified block diagram of a cardiac stimulator illustrated in FIG. 1 shows a first example of how the present invention may be implemented. In this drawing there is depicted schematically a heart 10 having a multi-electrode pacing/sensing lead 12 disposed therein. The lead 12 is shown as being passed through the superior vena cava and through the right atrium into the right ventricle with a distal tip electrode 14 located in the right apex and a proximal indifferent electrode 15 located outside of the heart. The lead 12 includes two intermediate ring electrodes 16 and 18 which are spaced along the length so that each resides in the right ventricle as illustrated.

Passing through the body of the lead 12 are a plurality of conductors indicated generally by numeral 20 for coupling the electrodes to an implantable stimulator device shown enclosed by dash line box 22.

The arrhythmia detection and stimulating apparatus enclosed by the dash line box 22 includes a first sense amplifier 24 having its input connected by a conductor 26 to the tip electrode 14 of the lead 12. The sense amplifier 24 is thus able to detect and amplify the QRS complex resulting from the beating action of the heart 10. The output from the sense amplifier 24 is fed to a pulse rate detector circuit 26 which, as its name implies, converts the R-R interval to a rate value, $R_1$. This measured heart rate value is then compared to a predetermined rate reference value $R_2$ as indicated by block 28 where the value $R_2$ is arbitrarily established as indicative of the onset of tachycardia. If it is determined as a result of the comparison that the measured rate $R_1$ is greater than the reference rate $R_2$ a signal is produced for partially enabling AND gate 30. This partial enable signal is merely indicative of an inordinately high ventricular rate, but at this point it could be due to either physiologic or pathologic causes. Thus, a means must be provided for determining whether, in fact, the high rate is due to pathologic origins requiring the stimulator to intervene to bring the heart rate back down to a safe level.

To confirm the diagnosis of pathologic tachycardia, the stimulator 22 includes circuitry 32 for detecting the preejection period of the heart. While various alternatives are available for implementing the PEP detect circuit 32, the invention depicted in FIG. 1 is based upon the use of an intracardiac impedance measurement in which a high frequency signal is applied via conductors 26 and 28 to the tip electrode 14 and the proximal electrode 16 of the lead 12. This causes a current to flow through the blood contained in the right ventricle and the resulting voltage changes occasioned by the influx and outflow of blood is sensed between the electrodes 16 and 18 and applied via conductors 36 and 38 to the PEP detector 32. As is explained in the Citek et al patent application Ser. No. 87,869, filed Aug. 21, 1987, and entitled "Physiologic Control of Pacemaker Rate Using Pre-ejection Interval as the Controlling Parameter", means are provided for accurately measuring PEP or a predetermined fraction thereof from the impedance waveform.

It is known from experiment on many patients during exercise that there is a direct correlation between PEP and the R-R cycle length and that as the heart rate goes up, there is a corresponding shortening in PEP. In particular, the formula $PEP = (cl + 84) \times 0.2$ rather accurately expresses the relationship. From this formula, it can be seen that for a 1 ms shortening of PEP, there is an approximate 5 ms shortening of R-R cycle length.

With continued reference to FIG. 1, block 40 receives as an input a ventricular rate value $R_1$ from the pulse rate detector 26 and functions to compute PEP based upon the measured cycle length using the above formula to produce a PEP value corrected for rate. This value is compared at block 42 with the actual PEP value being measured at block 32, with the compare circuit 42 producing an output on line 44 when the measured preejection period exceeds the expected pre-ejection period. Thus, the comparator 42 is effective to indicate whether measured PEP is appropriate for the current heart rate being sensed and, if not, applying a second input to the AND gate 30.

AND gate 30 will, of course, be fully enabled when it is determined that the measured heart rate exceeds a predetermined reference value and the pre-ejection period is longer than the corrected pre-ejection period for that rate. When the AND condition is satisfied, an enable signal is delivered to the cardiovert pulse generator which then becomes active to deliver a burst pattern of stimulating pulses to the ventricle, via the tip electrode 14, in an attempt to capture the heart and force its rate back to a rate which is commensurate with the level of physiologic activity of the subject. Cardioverter pulse generators, per se, are known in the art and it is not deemed necessary to set forth in detail herein the electronic design of such a pulse generator.

Because physiologic increments of heart rate are always accompanied by a corresponding decrease of PEP, it can be accurately inferred that if there is a fast rate accompanied by a relatively long PEP, the high rate is due to a non-physiologic tachycardia, e.g., a paroxysmal ventricular tachycardia due to a re-entry mechanism.

The use of intracardiac impedance measurements to derive PEP is only one way of sensing the length of the pre-ejection period. Alternative ways are also available. For example, the phasic opacification produced in the tissue by arterial blood flow can be detected by a photoplethysmograph in the manner explained in my earlier paper entitled "Densitography: A New Method for Evaluation of Cardiac Performance At Rest and During Exercise", published in the American Heart Journal, Vol. 83, pg. 493, 1972. Such a sensor may be placed anywhere in the vicinity of the pulse generator for as long as there is viable tissue between the light source, e.g., a light-emitting diode of the infrared type, and the photodetector. To preserve battery power, a window method of pulse detection is preferred as is the operation of the LED with a pulse of low duty cycle.

It is also contemplated that a solid-state pressure transducer appropriately positioned may serve as an indicator of the onset of the arterial pulse with the PEP being the interval between the occurrence of the electrical R-wave impulse and the onset of the mechanical arterial pulse. Rather than using a pressure transducer, a Doppler-type flow meter may be appropriately located over a major artery, e.g., the subclavian artery, with the onset of arterial blood flow corresponding to the start of eft ventricular ejection.

ALTERNATIVE EMBODIMENT

The embodiment of the invention illustrated in FIG. 1 can be improved upon as far as making the arrythmia diagnosis more specific by taking into account the rate at which heart rate is increasing (acceleration) and embodying that factor into the detection algorithm. Furthermore, a fibrillation detection logic is incorporated for initiating a large amplitude pulse for shocking the heart back into sinus rhythm. Such an arrangement is illustrated in the block diagram of FIG. 2. Here, an atrial (P-wave) or, alternatively, a ventricular (QRS-wave) sense circuit is identified by numeral 50 and a detector circuit 52 is coupled thereto for determining whether or not a P-wave (R-wave) is present. If not, the stimulator may be arranged to revert to its pacing mode (block 53) which may be either AAI, VVI or any of the other dual-chamber pacing modes.

If a P-wave (R-wave) is sensed by detector 52, the P-to-P (R-to-R) cycle length is measured at block 54 and a predetermined arbitrary number of successive intervals, e.g., six, are added and the composite length is stored as a value in A-register 56.

Figure 2:
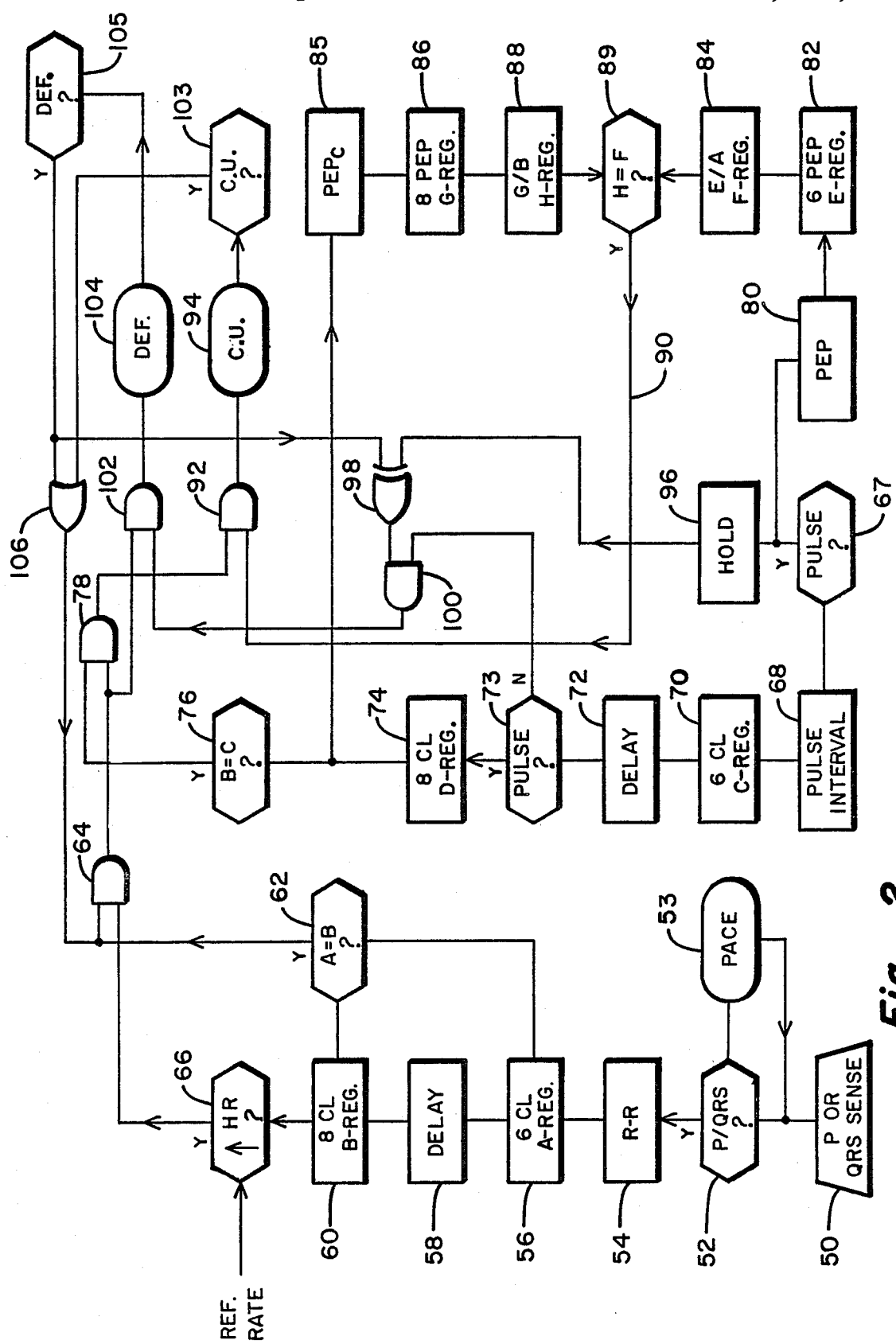
FIG. 2 is a block diagram of an alternative design for an antitachyarrhythmia cardiac stimulator.

Following a predetermined delay, represented by block 58, e.g., four to eight cycle lengths, another predetermined number of P-to-P or R-to-R cycle lengths, as the case may be, are summed and stored in the B-register 60. The number of cycle lengths stored in the B-register is intentionally made greater than the number stored in the A-register. In the drawing of FIG. 2, it is indicated that whereas six cycle lengths are stored in the A register, eight cycle lengths are stored in the B-register following the time delay established by block 58. Next, the contents of the A-register and the B-register 56 and 58, respectively, are compared as indicated by block 62. If it is determined that the value in the A-register is greater than or equal to that in the B-register, AND circuit 64 becomes partially enabled, indicating an abrupt rate.

That is, if the difference between the stored values in registers 56 and 60 is greater than 25 percent, it is implied that a sudden change has occurred and it is diagnosed as being abnormal by the output from comparator 62.

At the same time, the heart rate is compared as indicated by decision block 66 with a preset reference limit and if that limit is exceeded, a tachycardia is diagnosed. The gate 64 may then be fully enabled to reflect a "sudden-onset tachycardia".

Simultaneously with the P-wave (R-wave) detection by sensing circuit 50, a pulse detector 67 is used to sense a mechanical pulse occasioned by the beating action of the heart. In much the same way as the P-P (R-R) electrical interval is treated, a mechanical pulse-to-pulse cycle length or interval is measured at block 68 and a predetermined number of cycle lengths (cls) are summed and stored in C-register identified by numeral 70. At decision block 73, a test is made to determine if a mechanical pulse is present at a suitably positioned transducer and, if so, following a predetermined delay of an equal number of cardiac cycles as established by delay 58 introduced by delay circuit 72, a second predetermined number of pulse intervals are summed and stored in D-register 74. Again, a test for "suddenness" is carried out at decision block 76 to determine whether the total length of six pulse-to-pulse cycles stored in register 70 is greater than the total length of eight such cycles stored in register 74. If it is, it is indicative of a rapid rate increase and serves to corroborate the tachycardia detected by the electrical wave sensing operations previously described is real and not due to electrical interference, myopotentials or other spurious artifacts.

In the case of an atrial-operated mode, if A-V block exists during the supraventricular tachycardia, i.e., the ventricular rate is considerably slower than the atrial rate, the cardiac stimulator may to proceed to effect cardioversion unless otherwise programmed. On the other hand, a sudden increment of P-wave rate, together with a similar increment for the mechanical pulse rate partially enables AND gate 78 which becomes fully enabled when the AND condition of gate 64 is satisfied. The output from gate 78 thus signals the occurrence of a sudden-onset tachycardia which is corroborated by a signal of mechanical origin, i.e., the measured pulse rate.

To determine whether the rhythm being sensed responds to physiologic demand or is pathologic in nature, the system of FIG. 2 also includes means for measuring the pre-ejection period as reflected by block 80. A predetermined number (6) of such time intervals are added and stored in E-register identified by numeral 82 and the ratio of the PEP to the sum of six cycle lengths is obtained by dividing the contents of E-register 82 by the contents of A-register 56, leaving the result in F-register 84. Thus, F-register 84 is made to contain the basal PEP/CL relationship.

After the measurement of the sum of a plurality of PEPs and the capture of that value in E-register 82 and the expiration of delay period 72, a predetermined greater number PEPs (e.g., eight) are corrected for rate at block 85, summed and held in G-register 86.

At this point, the content of G-register 86 is divided by the contents of the B-register 60 to again obtain a basal PEP to cycle length ratio and the resulting quotient is stored in H-register 88. This value is compared to the content of F-register 84, as represented by decision block 89 in FIG. 2, and a determination is made as to whether or not a significant shortening of PEP has occurred over a relatively short period of time. If it is found that the contents of H-register is greater than the contents of F-register, it is known that the change in PEP has been under 25 percent and a signal will appear on line 90 connected as a first input to AND circuit 92.

The second input to AND gate 92 comes from the output of AND gate 78. It will be recalled that gate 78 is fully enabled when there has been a rapid onset of a high pulse rate and the heart rate is found to exceed a predetermined rate threshold indicative of tachycardia. Thus, when those events are likewise accompanied by an inappreciable increase or shortening in PEP, as determined at decision block 89, cardiovert pulse generator 94 will be activated to generate a burst of timed pulses for capturing the heart and dropping the rate to a value appropriate for the physiologic state of the patient at the time.

The output from the pulse transducer 67 is captured in a sample-and-hold circuit 96 and the output of that circuit is applied as a first input to EX-OR gate 98. The resulting output thereof is fed to a first input of AND gate 100 whose second input comes from the pulse detector 73. If no pulse is detected at 73, AND gate 100 will be fully enabled to apply a logic signal to a further AND gate 102. The second input to AND gate 102 arrives from the output of AND gate 64. It will be recalled that gate 64 becomes enabled when a sudden rate increase is detected and the resulting rate is above the threshold established at decision circuit 66. It can be seen, then, that the gate 102 will be fully enabled when the heart rate is inordinately high and a once-present pulse disappears. Such a condition is indicative of ventricular fibrillation and the output of gate 102 is used to trigger defibrillator circuit 104 to cause a DC defibrillation shock to be delivered to the heart between, for example, a patch electrode and an indifferent electrode.

If either the cardioversion circuit 94 or the defibrillator circuit 104 is activated as determined at decision blocks 103 and 105, OR circuit 106 is activated to permit a repetition of the discharge where the electrical (QRS) rate tested at 66 remains high. The number of subsequent defibrillatory shocks or cardioversion bursts can be made a programmable feature.

It can be seen, then, in the embodiment of FIG. 2, the underlying diagnosis of pathologic tachycardia is achieved by observing a rate increase above a pre-established threshold not accompanied by a concurrent shortening of PEP. It is confirmed by simultaneously observing the manner in which the mechanical pulse rate changes. Moreover, the element of rate of change of rate and rate of change of PEP is also factored into the algorithms to enhance the reliability of the decision whether to initiate cardioversion because the tachycardia being sensed is pathologic or whether to forego application of a cardioverting burst where physiologic tachycardia is indicated.

It is also deemed to be advantageous to be able to program the number of cycle lengths to be measured and stored in the registers 56 and 60 as well as the pulse cycle lengths to be stored in registers 70 and 74. This allows the algorithm to be adjusted to the particular type of arrythmia found in different patients.

Persons skilled in the art will readily recognize how the algorithms reflected in FIGS. 1 and 2 of the drawings may be implemented using integrated circuit technology. Thus, it is believed unnecessary to describe in detail the electronics for performing the interval measurement steps, the summation of cycle lengths, the comparison of stored values and the like.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. Apparatus for detecting tachycardia in a living subject for initiating cardioversion means when determined to be pathologic rather than physiologic in nature, comprising:
   (a) means for measuring the pulse rate of a beating heart and developing a first control signal value proportional thereto;
   (b) means for comparing said first control signal value to a pre-established heart rate value for said subject and developing a second control signal value when said first control signal value exceeds said pre-established heart rate value;
   (c) means for sensing the pre-ejection period of said subject's heart and developing a third control signal value proportional thereto;
   (d) means for comparing said third control signal value with a fourth control signal value proportional to a rate corrected pre-ejection period value of said subject's heart based upon its current heart rate and producing a fifth control signal value when said third control signal value exceeds said fourth control signal value; and
   (e) means for sensing coincidence of said second and fifth control signal values for initiation of said cardioversion means.

2. Antitachyarrythmia pacing apparatus for producing cardioverting pulse patterns for application to a subject's heart upon detection of tachycardia of pathologic origin, comprising:
   (a) means coupled to the heart for sensing an existing pulse rate;
   (b) means coupled to said sensing means for comparing said pulse rate to a pre-established pulse rate value for said subject, with the comparing means providing an indication when the sensed pulse rate exceeds the pre-established pulse rate;

(c) means for measuring the pre-ejection period of the subject's heart;

(d) means responsive to said measuring means for indicating whether said measured pre-ejection period exceeds a corrected value for the subject's pulse rate; and (e) means coupled to said means for comparing and said means for indicating for initiating generation of said cardioverting pulse patterns only when said sensed pulse rate exceeds the pre-established pulse rate and said measured prejection period exceeds and expected value.

3. Antitachyarrythmia pacing apparatus for producing cardioverting pulse patterns for application to a subject's heart upon detection of tachycardia of pathologic origin, comprising:

(a) means coupled to the heart for sensing an existing pulse rate;

(b) rate of change detecting means coupled to said sensing means for determining the rate of increase of pulse rate over a predetermined time interval;

(c) first comparison means coupled to said sensing means for comparing said pulse rate to a pre-established pulse rate value for said subject, with the first comparison means providing signal indication when the sensed pulse rate exceeds the pre-established pulse rate;

(d) gating means for producing a given output when said first comparison means provides said signal indication and said rate of change detecting means senses a rate change exceeding a predetermined value;

(e) means for measuring the pre-ejection period of the subject's heart;

(f) second comparison means responsive to said measuring means for indicating whether said measured pre-ejection period exceeds an expected value for the subject's then pulse rate; and (g) means coupled to said gating means and said second comparison means for initiating generation of said cardioverting pulse patterns only when said gating means produces said given output and said measured pre-ejection period exceed said expected value.

4. Antitachyarrythmia pacing apparatus for producing cardioverting pulse patterns for application to a subject's heart upon detection of tachycardia of pathologic origin, comprising:

(a) means for sensing heart depolarization signals;

(b) first means coupled to said sensing means for measuring the total cycle length between a first predetermined number of successive heart depolarization signals;

(c) second means coupled to said sensing means for measuring the total cycle length between a second predetermined number of successive depolarization signals, said second number being greater than said first number and the second measurement being delayed a predetermined time from the first measurement;

(d) first comparator means for producing an output when said first measurement exceeds said second measurement;

(e) second comparator means for producing an output when the rate at which heart depolarization signals being sensed exceeds a predetermined rate value;

(f) first gating means coupled to receive the output from said first and second comparator means and producing an output only when said output from said first and second comparator means are simultaneously present;

(g) pre-ejection period sensing means for measuring the pre-ejection interval of the heart;

(h) means coupled to said first means and to the pre-ejection period sensing means for detecting changes in length of the pre-ejection period with changes in cycle length;

(i) cardioverter pulse producing means for applying a predetermined pattern of electrical pulses to the heart; and (j) further gating means coupling said cardioverter pulse producing means to the output of said first gating means and said means for detecting changes in length of the preejection period.

5. A method for detecting the occurrence of a pathologic tachycardia in a living subject comprising the steps of:

(a) measuring the heart rate of said subject;

(b) measuring the pre-ejection period of the subject's heart; and (c) detecting when the heart rate exceeds a predetermined rate reference value while the pre-ejection period remains relatively fixed in length.

6. The method as in claim 5 and further including the steps of:

(a) calculating an expected pre-ejection period based upon the existing heart rate;

(b) comparing the expected pre-ejection period with the measured pre-ejection period; and (c) determining from the comparison whether the measured pre-ejection period is varying with changes in heart rate.

* * * * *

UNITED STATES PATENT AND TRADEMARK OFFICE
CERTIFICATE OF CORRECTION

PATENT NO. : 4,865,036

DATED : September 12, 1989

INVENTOR(S) : Raul Chirife

It is certified that error appears in the above-identified patent and that said Letters Patent is hereby corrected as shown below:

Column 9, line 11, change "prejection" to -- pre-ejection--.

Column 9, line 12, change "and" to -- an --.

Column 9, line 44, change "exceed" to -- exceeds --.

Signed and Sealed this

Twenty-fifth Day of September, 1990

*Attest:*

HARRY F. MANBECK, JR.

*Attesting Officer*     *Commissioner of Patents and Trademarks*